United States Patent
Deitch et al.

(10) Patent No.: US 9,820,772 B2
(45) Date of Patent: *Nov. 21, 2017

(54) VAGINAL MANIPULATOR WITH A HEAD EXTENDER

(71) Applicant: Coloplast A/S, Humlebaek (DK)

(72) Inventors: Sarah J. Deitch, Minneapolis, MN (US); Ty Erickson, Idaho Falls, ID (US); Allen Gaynor, Coon Rapids, MN (US); Jeffrey Brian Taylor, Forest Lake, MN (US); Michael M. Witzmann, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 224 days.

This patent is subject to a terminal disclaimer.

(21) Appl. No.: 14/798,465

(22) Filed: Jul. 14, 2015

(65) Prior Publication Data

US 2015/0313637 A1    Nov. 5, 2015

Related U.S. Application Data

(63) Continuation of application No. 14/138,145, filed on Dec. 23, 2013, now Pat. No. 9,186,178, which is a continuation of application No. 13/772,378, filed on Feb. 21, 2013, now Pat. No. 8,690,893.

(60) Provisional application No. 61/684,822, filed on Aug. 20, 2012.

(30) Foreign Application Priority Data

Aug. 16, 2012    (DK) .................................. 2012 00506

(51) Int. Cl.
*A61B 17/42*  (2006.01)
*A61B 17/02*  (2006.01)
*A61B 17/00*  (2006.01)
*A61B 90/00*  (2016.01)

(52) U.S. Cl.
CPC .......... *A61B 17/42* (2013.01); *A61B 17/0218* (2013.01); *A61B 17/4241* (2013.01); *A61B 90/03* (2016.02); *A61B 2017/00849* (2013.01); *A61B 2017/4216* (2013.01); *A61B 2017/4225* (2013.01); *A61B 2090/037* (2016.02)

(58) Field of Classification Search
CPC ................ A61B 17/42; A61B 17/4241; A61B 2017/4216; A61B 2017/4225
See application file for complete search history.

(56) References Cited

U.S. PATENT DOCUMENTS 7,070,561 B1    7/2006  Ansari
2007/0038216 A1    2/2007  Hamada

FOREIGN PATENT DOCUMENTS

WO    03077770 A1    9/2003

*Primary Examiner* — Robert Lynch
(74) *Attorney, Agent, or Firm* — Coloplast Corp., Coloplast A/S; Nick Baumann

(57) ABSTRACT

A vaginal manipulator includes a head, a tissue index, a door, and a head extender. The head has a first end connected to a shaft and a distal end opposite of the first end. The tissue index is disposed laterally across the head and is adapted to slide in a longitudinal direction between the first end and the distal end of the head. The door has a pivot portion attached to a distal portion of the head and a free portion that is movable away from the head. The head extender includes a post that is insertable into an orifice formed in the distal end of the head.

14 Claims, 16 Drawing Sheets

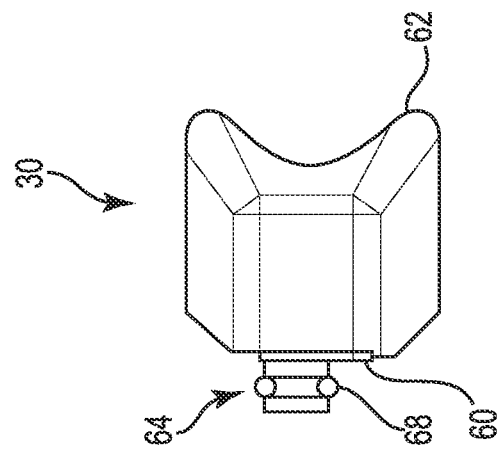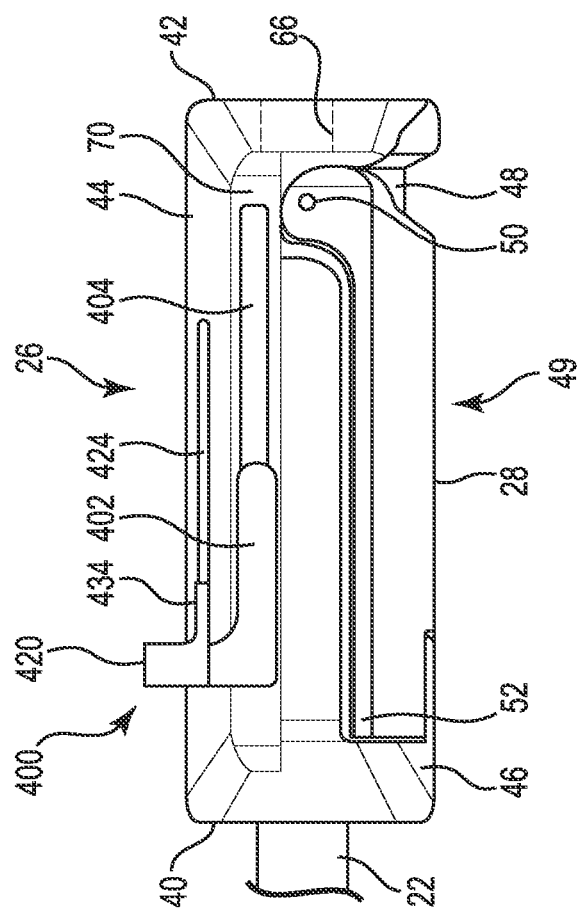
Fig. 2

VAGINAL MANIPULATOR WITH A HEAD EXTENDER

BACKGROUND

There is a trend to move toward minimally invasive surgical procedures that allow the patient to recover faster. Faster recoveries are associated with less time in post anesthesia and other care units, which can translate to a lower cost of patient care.

Many such minimally invasive surgical procedures are performed laparoscopically through multiple access ports formed in the abdomen. At least one access port is formed to provide access for a camera that allows visualization of the internal organs, and at least one access port is formed to provide surgical tools with access to the internal organs. However, it is often the case that the organ selected for surgical intervention will have a surface that is oriented away from the camera such that the surgeon has an imperfect view of the complete organ.

Surgeons would welcome a new device for manipulating the orientation of internal organs to provide a better view and access to all surfaces of the organ.

SUMMARY

One aspect provides a vaginal manipulator including a head with a tissue index, a door, and a head extender that are attached to the head. The head has a first end connected to a distal end of a shaft and a distal end opposite of the first end, an anterior side opposite a posterior side, a first lateral edge extending between the anterior and posterior sides, and a second lateral edge extending between the anterior and posterior sides. The tissue index has a first arm that is slidingly engaged with a first groove formed in the first lateral edge of the head, a second arm that is slidingly engaged with a second groove formed in the second lateral edge of the head, and a rib connected between the first and second arms and disposed laterally across the anterior side of the head. The door is coupled to and movable relative to the posterior side of the head. The head extender is removably attached to the distal end of the head.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a side view of the head extender separated from the head.

DETAILED DESCRIPTION

Figure 1:
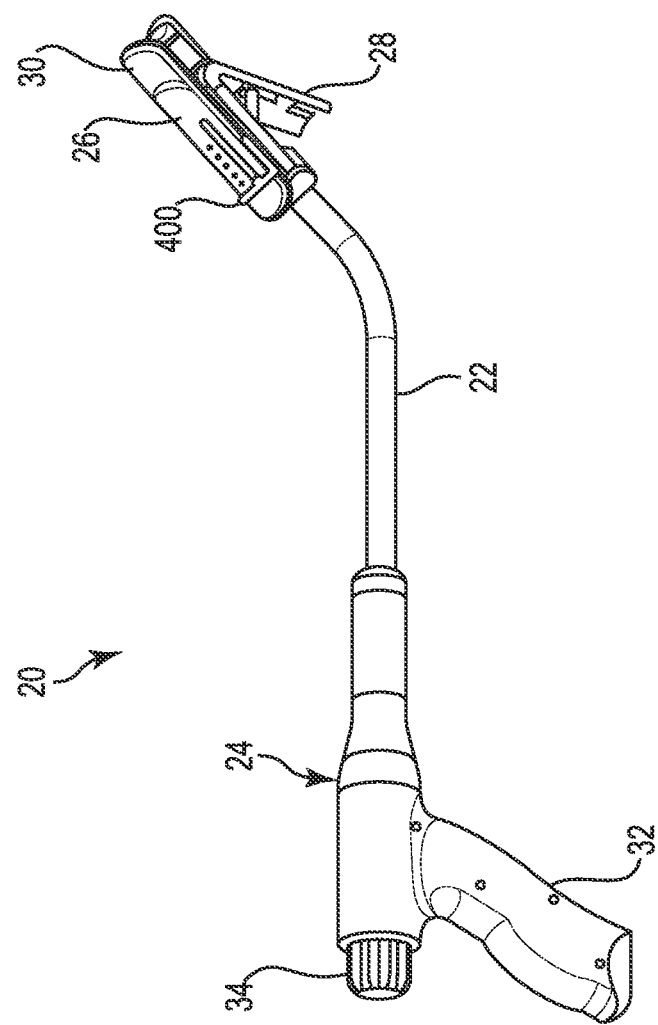
FIG. 1 is a perspective view of one embodiment of a vaginal manipulator including a head with a head extender and a tissue index attached to the head.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Anterior means "forward" or "front," and posterior means "rearward" or "back" relative to the patient. For example, relative to surfaces of an organ in the human body, an anterior side is oriented forward toward the belly and a posterior side is oriented rearward toward the spine.

Individuals have anatomy of different sizes. For example as regards females, the vaginal vault can vary in length (depth). Some women having had a hysterectomy will have all or some of the cervix removed (e.g., a cervical stump is at times left in place at the apex of the vagina). Embodiments provide a surgical device having a head that is useful in manipulating walls of the vagina and portions of the cervix (if present). The head includes a door (or a kick-out door)

that can be deployed to move a posterior wall of the vagina into a line of sight of a surgeon during a laparoscopic procedure. The device includes a head extender that provides improved manipulation and control of the apex of the vagina, independent of the length of the vagina. Embodiments of the head extender allow the device to accommodate vaginal vaults of varying sizes.

The surgical device is useful in gynecological, colorectal and other procedures. The surgical device may be manually deployed into an organ during an open procedure. The surgical device may be employed in a laparoscopic procedure or robotically manipulated in a robotically-assisted surgical procedure.

For example, in a laparoscopic procedure a camera system is inserted into a camera port formed through the wall of the abdomen to allow visualization of the internal organs. Other ports are formed in the abdomen to allow tools and devices to access a selected organ. The selected organ will have a surface oriented toward the camera (an anterior side) and a surface away from the camera (a posterior side). The head of the surgical device is provided with a movable surface that operates to present or displace the posterior side of the selected organ in a direction for improved visualization by the camera. This feature is particularly useful when manipulating a posterior wall of the vagina that is typically oriented to face away from the abdomen and away from a camera that is inserted into the abdomen laparoscopically.

Embodiments provide an organ expansion device that is useful for manipulating a vagina, a uterus, a rectum, or an esophagus for improved access during minimally invasive surgical (laparoscopic or robotic) procedures.

FIG. 1 is a perspective view of one embodiment of a vaginal manipulator 20. The vaginal manipulator 20 (manipulator 20) includes a shaft 22 connected between a handle 24 and a head 26, with a door 28, a head extender 30, and a sliding tissue index 400 attached to the head 26. The handle 24 includes a grip feature 32 and an actuator 34. The handle 24 provides a control surface or a grip for the surgeon (or assistant) to grab during use of the manipulator 20. The actuator 34 is connected with the door 28 to allow the surgeon to move the door 28 open/closed (out/in) relative to the head 26.

In one embodiment, the shaft 22 is a rigid shaft formed from a metal tube, such as stainless steel tube. In one embodiment, the shaft 22 is substantially straight and is provided without a bend or bend angle. In one embodiment, the shaft 22 is curved to include a bend as illustrated in FIG. 1 having an angle in the range from about 5-90 degrees, with one acceptable angle being about 45 degrees. In one embodiment, the shaft 22 is curved such that a top side (or anterior side) of the head 26 is closer to the handle 24 than a bottom side (or posterior side) of the head 26 is to the handle 24. The curved shaft 22 is adapted to orient the vagina in its natural location for a patient in surgery while at the same time orienting the handle 24 in a comparable position for manipulation by the surgeon.

In one embodiment, the rigid shaft 22 is fabricated to plastically deform (fail) at a bending force of 20 pounds. The shaft 22 is designed to carry loads and bending forces of less than 20 pounds. The shaft 22 is designed to noticeably deform/fail when the bending force is greater than 20 pounds. This feature allows the manipulator 20 to move/orient the vagina during surgery while preventing the operating room staff from unintentionally delivering an undesirably large force to the patient during surgery.

The shaft 22 encloses portions of the actuator 34 that extend from the handle 24 to the head 26. In some applications, it is desirable that the shaft 22 is rigid to allow the surgeon to have a one-to-one correlation between movement of the handle 24 and movement of the head 26. In addition, a rigid shaft 22 allows the surgeon to use the device 20 as a lever in moving tissue or in adjusting a location of an organ within the body.

The handle 24 is a molded plastic or metal structure. In one embodiment, the handle 24 is provided as a two-piece clamshell structure that is fitted in a mating arrangement around the shaft 22 and portions of the actuator 34. The housing 30 and the grip feature 32 are elongated to provide surfaces that the surgeon may grasp during retroversion of the vagina or other organ.

The actuator 34 operates to move the door 28 and can include a knob or a sliding feature that is suitably connected with a linkage attached to the door 28. One suitable actuator 34 assembly is described below with reference to FIG. 11. One suitable linkage includes an arm assembly pinned between the door 28 and the head 26, where the pin(s) allow the arm assembly to rotate as the door 28 moves relative to the head 26.

The sliding tissue index 400 is manually movable to different positions along the head 26 for placement at a selected distance away from the leading (distal) end of the head 26 (or the head extender 30 if attached).

FIG. 2 is a side view of the head extender 30 separated from the head 26. In one embodiment, the head 26 includes a proximal end 40 that is connected to the shaft 22 opposite a distal end 42, an anterior side 44 opposite a posterior side 46, with a recess 48 formed in the posterior side 46. The door 28 is formed to smoothly mate or nestle within the recess 48. In one embodiment, the door 28 includes a pivot portion 50 that is connected to the head 26 and a free portion 52 opposite the pivot portion 50. In one embodiment, the pivot portion 50 is attached to the opposed side edges of the head 26 and the free portion 52 is movable into and out of the recess 48. The door 28 is movable between a stowed position (illustrated) in which the door 28 is disposed in the recess 48 and an extended position in which the door 28 pivots away from the posterior side 46 of the head 26. In the illustrated stowed position, the door 28 provides the head 26 with a substantially smooth posterior surface 49 that is configured to reduce or prevent the head 26 from pinching tissue.

The head extender 30 is attachable to the head 26 to provide the manipulator 20 with an adjustable head length. In one embodiment, the head extender 30 has a proximal end 60 opposite a distal end 62 and a post 64 extending from the proximal end 60 that is insertable into an orifice 66 formed in the distal end 42 of the head 26. The post 64 engages with the orifice 66 and allows the head extender 30 to be attached/removed relative to the head 26 as desired by the surgeon. In one embodiment, the post 66 includes a seal feature 68 provided to ensure secure engagement between the head extender 30 and the head 26. One suitable seal feature 68 includes a silicone or a rubber o-ring.

In one embodiment, the manipulator 20 is a disposable surgical device and is fabricated to include a plastic handle 24 and a plastic head 26 attached to a stainless steel shaft 22. Suitable plastics for fabricating the head 26 include nylon, polypropylene, polyethylene, polyester, or other suitable plastic materials. The head extender 30 can be disposed of and is likewise fabricated from one of these suitable plastics. In another embodiment, all components of the manipulator 20 are reusable and are fabricated from a suitable material such as stainless steel. The tissue index 400 is suitably fabricated from metal such as stainless steel or plastic, for example nylon, polypropylene, polyethylene, polyester, or other plastic material.

In one embodiment, the post 64 allows the head extender 30 to snap-fit into the orifice 66 formed in the distal end 42 of the head 26 to provide manual push-in and pull-out attachment of the head extender 30 to the head 26.

In one embodiment, the head extender 30 engages the orifice 66 formed in the distal end 42 of the head 26 and includes a release mechanism that is operable to detach the head extender 30 from the head 26.

In one embodiment, the head extender 30 is provided as a separate device for use with the device 20, or alternatively, one or more head extenders 30 are provided with the device 20 in the form of a kit of parts.

The sliding tissue index 400 is movable along the anterior side 44 of the head 26 and includes a first arm 402 that is slidingly engaged with a first groove 404 formed in a first lateral edge 70 of the head 26, a second arm 412 that is slidingly engaged with a second groove 414 formed in a second lateral edge 72 of the head 26 (See FIG. 3), and a rib 420 connected between the first and second arms 402, 412 and disposed laterally across the anterior side 44 of the head 26. In one embodiment, the sliding tissue index 400 is engaged with both opposed lateral edges 70, 72 and the anterior side 44 of the head 26, which ensures robust engagement of the index 400 to the head 26 as the head 26 is introduced into and withdrawn from the vagina.

Figure 3:
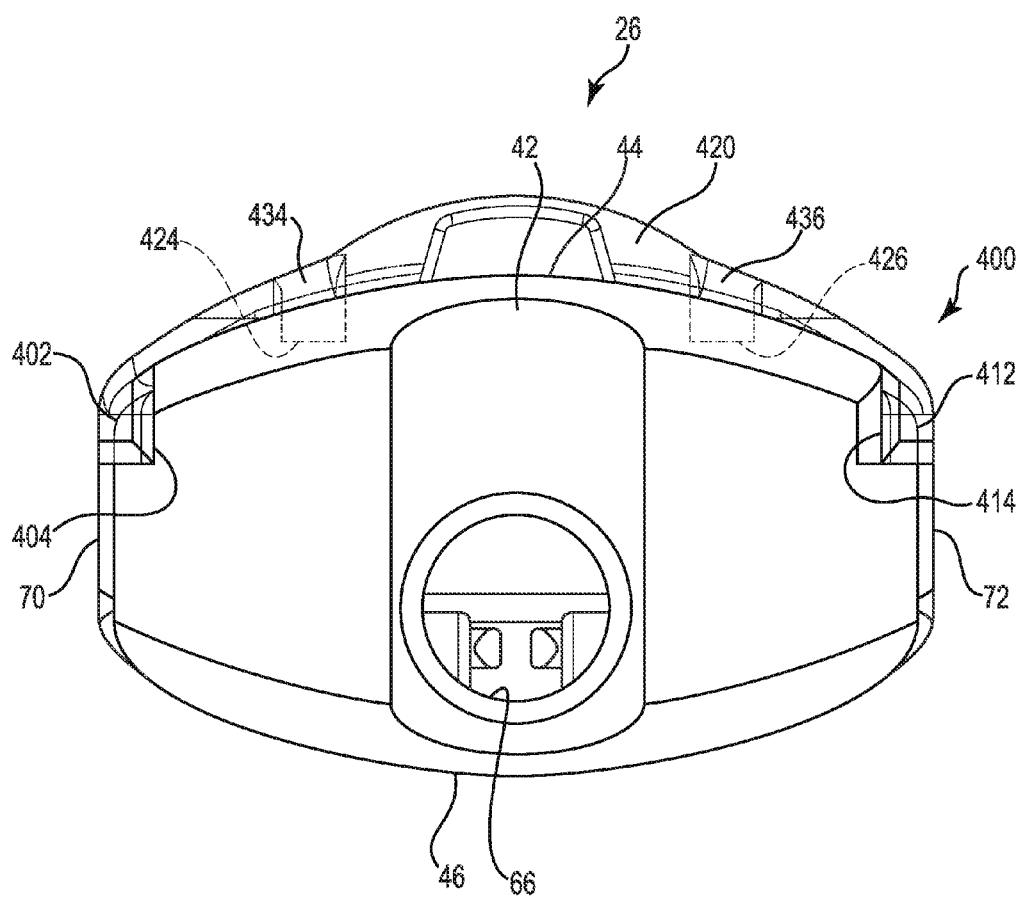
FIG. 3 is a distal end view of the head illustrated in FIG. 2.

In one embodiment, the tissue index 400 is supported by a guide feature formed in the anterior side 44 of the head 26 as described in FIG. 3.

Figure 4:
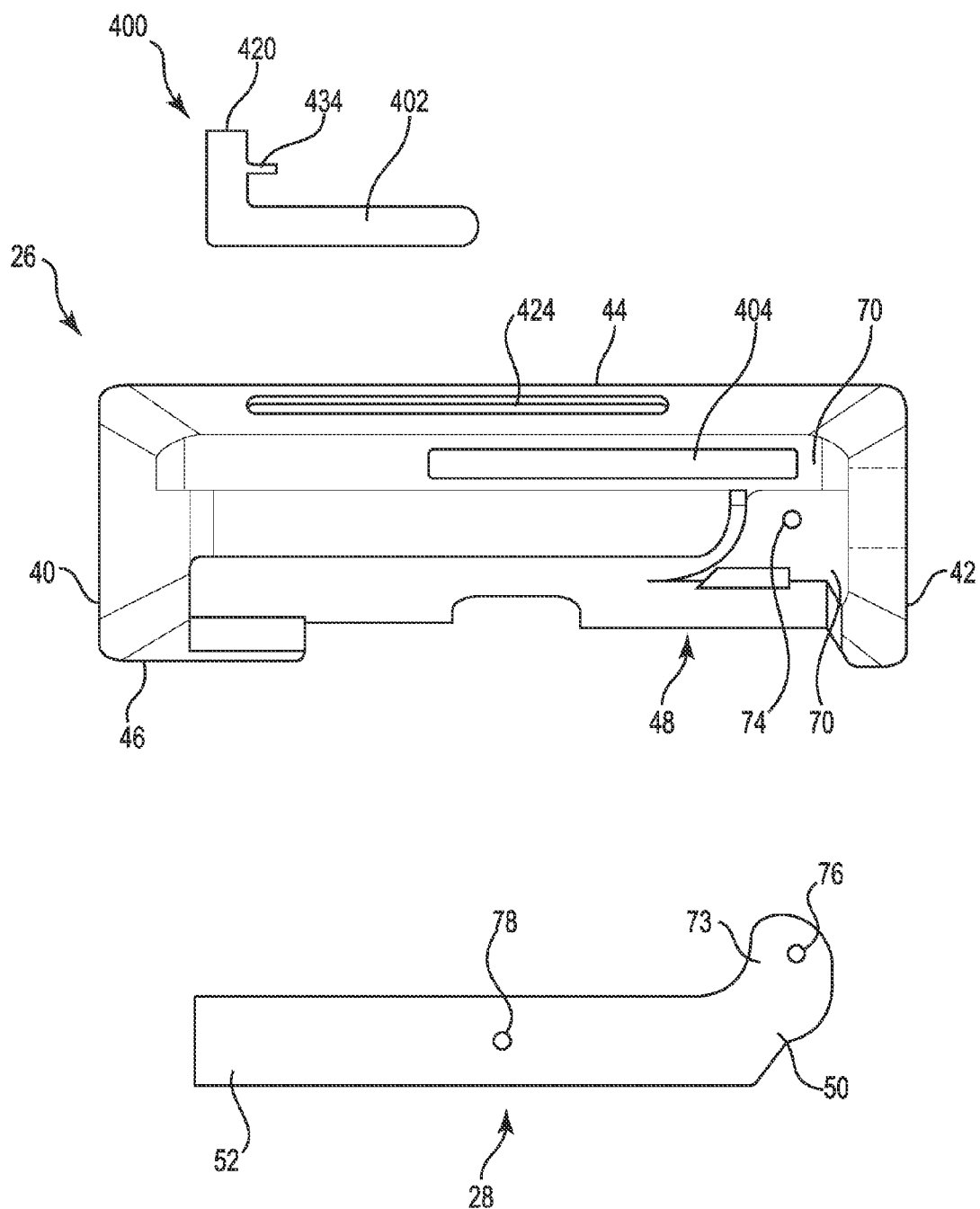
FIG. 4 is a side view of the head with a door and a tissue index detached from the head.

FIG. 3 is an end view of the head 26 and FIG. 4 is a side view of the door 28 displaced from the head 26. In one embodiment, the head 26 has opposing lateral edges 70, 72 located between the proximal end 40 and the distal end 42. The pivot portion 50 of the door 28 is provided with opposing door flanges 73 that attach to the opposing lateral edges 70, 72 of the head 26. For example, each of the lateral edges 70, 72 is provided with a pin 74 extending from the lateral edge, and each of the door flanges 73 is provided with a recess 76 or opening 76 that is sized to receive the pin 74. The mechanism of the actuator 34 (FIG. 1) includes a linkage that is coupled to the door 28 at an engagement location 78. The actuator 34 is operable to move the linkage and thus the door 28, and the pivot portion 50 is configured to rotate about the pins 74 to allow the free portion 52 of the door 28 to move into and out of the recess 48.

The rib 420 of the sliding tissue index 400 is movable to different positions along the anterior side 44 of the head 26 and is assisted by a guide feature. The guide feature is provided by a guide (434 or 436) that slides in a groove (424 or 426, respectively). In an exemplary embodiment, the anterior side 44 of the head 26 is formed to provide a first longitudinal groove 424 parallel to a second longitudinal groove 426 and the rib 420 of the tissue index 400 includes a first guide 434 positioned to slide in the first longitudinal groove 424 and a second guide 436 positioned to slide in the second longitudinal groove 426. The guide feature provides the sliding tissue index 400 with side-to-side and longitudinal stability as the index 400 is moved along the head 26.

Figure 5:
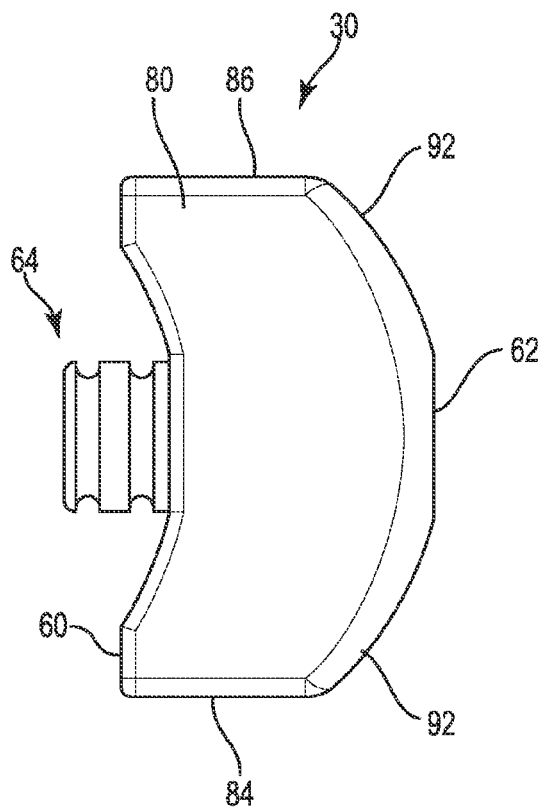
FIG. 5 is a top view and FIG. 6 is a side view of the head extender.
Figure 6:
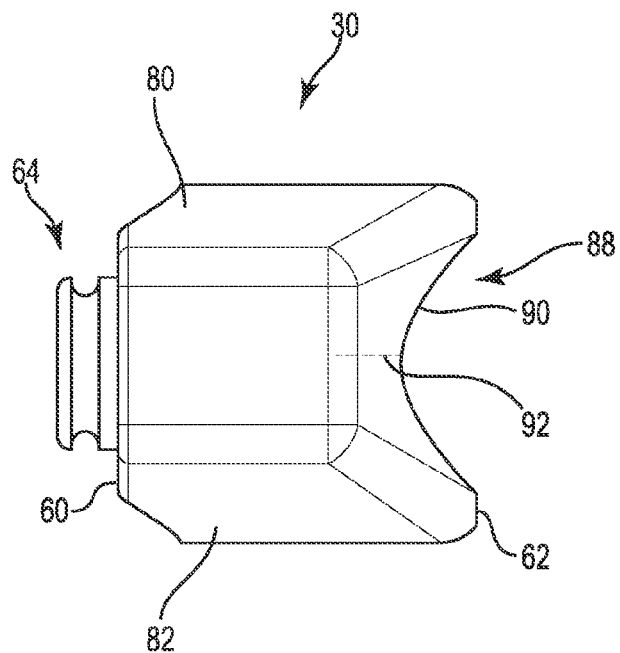
Figure 7:
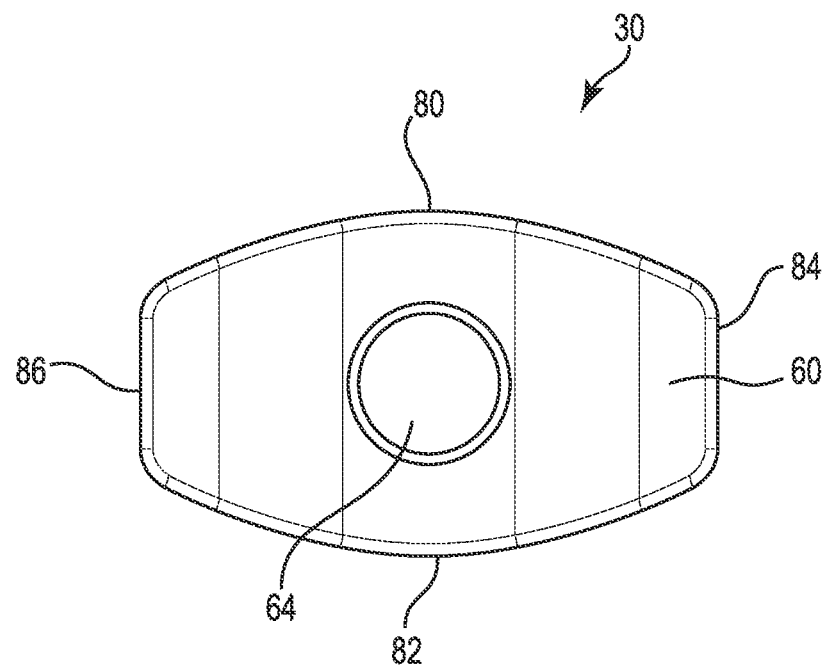
FIG. 7 is a proximal end view and FIG. 8 is a cross-sectional view of the head extender.
Figure 8:
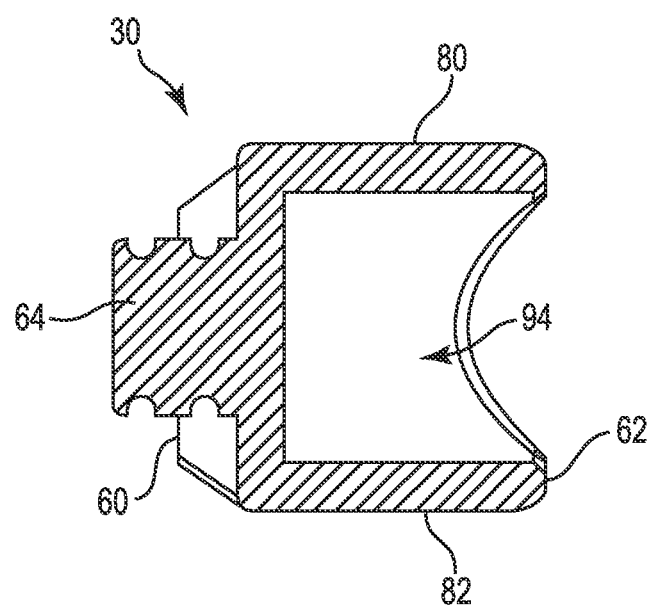

FIG. 5 is a top view, FIG. 6 is a side view, FIG. 7 is a proximal end view, and FIG. 8 is a cross-sectional view of the head extender 30.

With reference to FIG. 5 and FIG. 6, the head extender 30 includes a top surface 80 opposite a bottom surface 84 and planar lateral edges 84, 86 that extend between the proximal end 60 and the distal end 62. With additional reference to FIG. 7, the top surface 80 in the bottom surface 82 of the head extender 30 are curved in a smooth convex manner and are blended with the planar lateral surfaces 84, 86.

With reference to FIG. 5 and FIG. 6, in one embodiment the distal end 62 of the head extender 30 provides a compound curvature 88. The compound curvature 88 includes a concave curvature 90 that intersects with a convex curvature 92. For example, the compound curvature 88 includes the convex curvature 92 when viewed from the top (FIG. 5) and the concave curvature 90 when viewed from the side (FIG. 6). The compound curvature 88 of the head extender 30 thus presents a saddle structure with the concave curvature 90 curving and connecting with the top and bottom surfaces 80, 82 and the convex curvature 92 curving and connecting with the opposed lateral edges 84, 86.

FIG. 8 is a cross-sectional view of the head extender 30 illustrating a pocket 94 formed in the distal end 62. In one embodiment, the pocket 94 provides a cervical cup that is sized and configured to receive a fornix of the cervix of the female patient. The compound curvature 88 formed at the distal end 62 of the head extender 30 allows the head extender 30 to engage with the interior apex of the vagina, and the pocket 94 is adapted to receive the fornix portion of the cervix in a manner that provides excellent control when manipulating walls of the vagina.

The pocket 94 is useful to accommodate those patients that retain all of or some portion of their cervix. However, some patients having had a hysterectomy no longer have a cervix. With this in mind, embodiments of the head extender 30 include a cap or a plug (not shown) that is sized to be inserted into the pocket 94 to provide the head extender 30 with a smooth rigid surface along the distal end 62. It is preferable that when the head extender 30 is provided with the cap or the plug that the compound curvature 88 is maintained.

Figure 9:
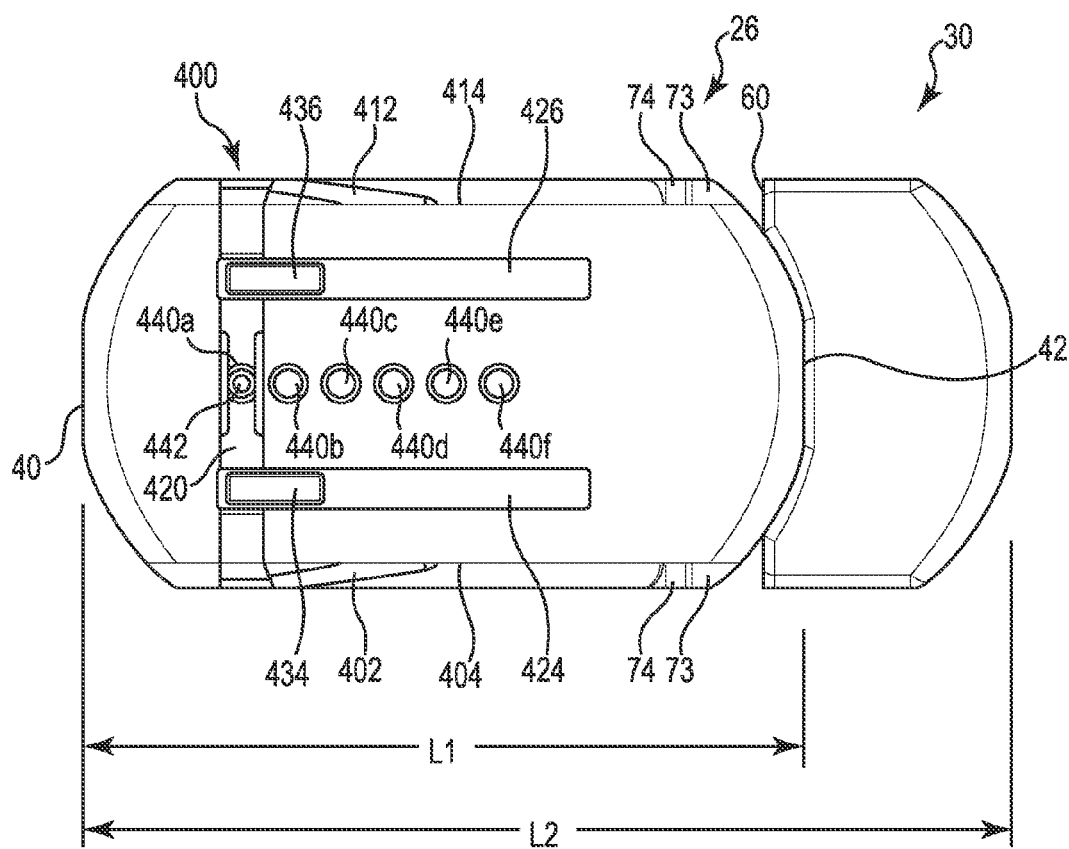
FIG. 9 is a top view of the head extender and the tissue index attached to the head.
Figure 10:
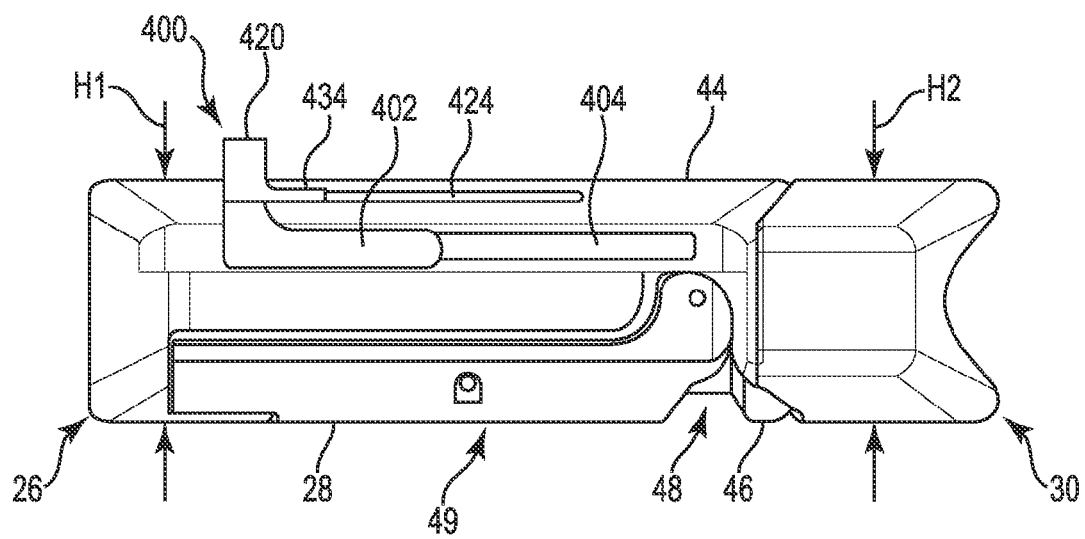
FIG. 10 is a side view of the head extender and the tissue index attached to the head with the door in a closed position.

FIG. 9 is a top view and FIG. 10 is a side view of the head extender 30 attached to the head 26. In one embodiment, the head 26 has a head length L1 extending between the proximal end 40 and the distal end 42 and the head extender 30 attaches to the head 26 to effectively extend the head length L1 by approximately 10-35% to a new extended length L2. When the head extender 30 is attached to the head 26, the extended length L2 extends the head length L1 by a distance of about 1-5 cm. In one exemplary embodiment, the head length L1 is about 7 cm and the head extender 30 has a length of about 2 cm such that the extended length L2 is about 9 cm.

In one embodiment, the head 26 has a head height H1 extending between the anterior side 44 and the posterior side 46 and the head extender 30 has a head height H2 that is substantially equal to the head height H1.

It is desirable that the head extender 30 fits tightly against the head 26 in a complementary manner to reduce the possibility of creating a skin pinch-point between the head 26 and extender 30. With reference to FIG. 9, in one embodiment a convex curvature at the distal end 42 of the head 26 is complementary (e.g. is shaped to have a similar radius of curvature) to a concave curvature at the proximal end 60 of the head extender 30.

In one embodiment, the head 26 is formed to provide a series of recessed cups 440a, 440b, . . . 440f, aligned along a longitudinal axis of the anterior side 44 of the head 26 and the rib 420 of the tissue index includes a prong 442 that is sized for placement into each one of the recessed cups 440a, 440b, . . . 440f. In the illustrated embodiment of FIG. 9, the prong 442 is seated or engaged with the recessed cup 440a to position the rib 420 of the tissue index 400 at a furthest distance away from the distal end 42 of the head 26.

The sliding tissue index 400 is moved by lifting the rib 420 away from the anterior side 44 of the head 26 and sliding the arms 402, 412 within their respective grooves 404, 414 and sliding the guides 434, 436 in their respective grooves 424, 426. When the tissue index 400 is at the desired location determined by the surgeon, for example, the prong 442 is placed in the nearest one of the recessed cups 440a, . . . 440f.

In one embodiment, the tissue index 400 extends laterally across the anterior side 44 of the head 26 in a straight line between the lateral edges 70, 72. In one embodiment, the tissue index 400 extends laterally across the anterior side 44 of the head 26 in a smooth curve extending between the lateral edges 70, 72.

With reference to FIG. 10, the door 28 fits into the recess 48 to provide the head 26 with a substantially smooth posterior surface 49.

Figure 11:
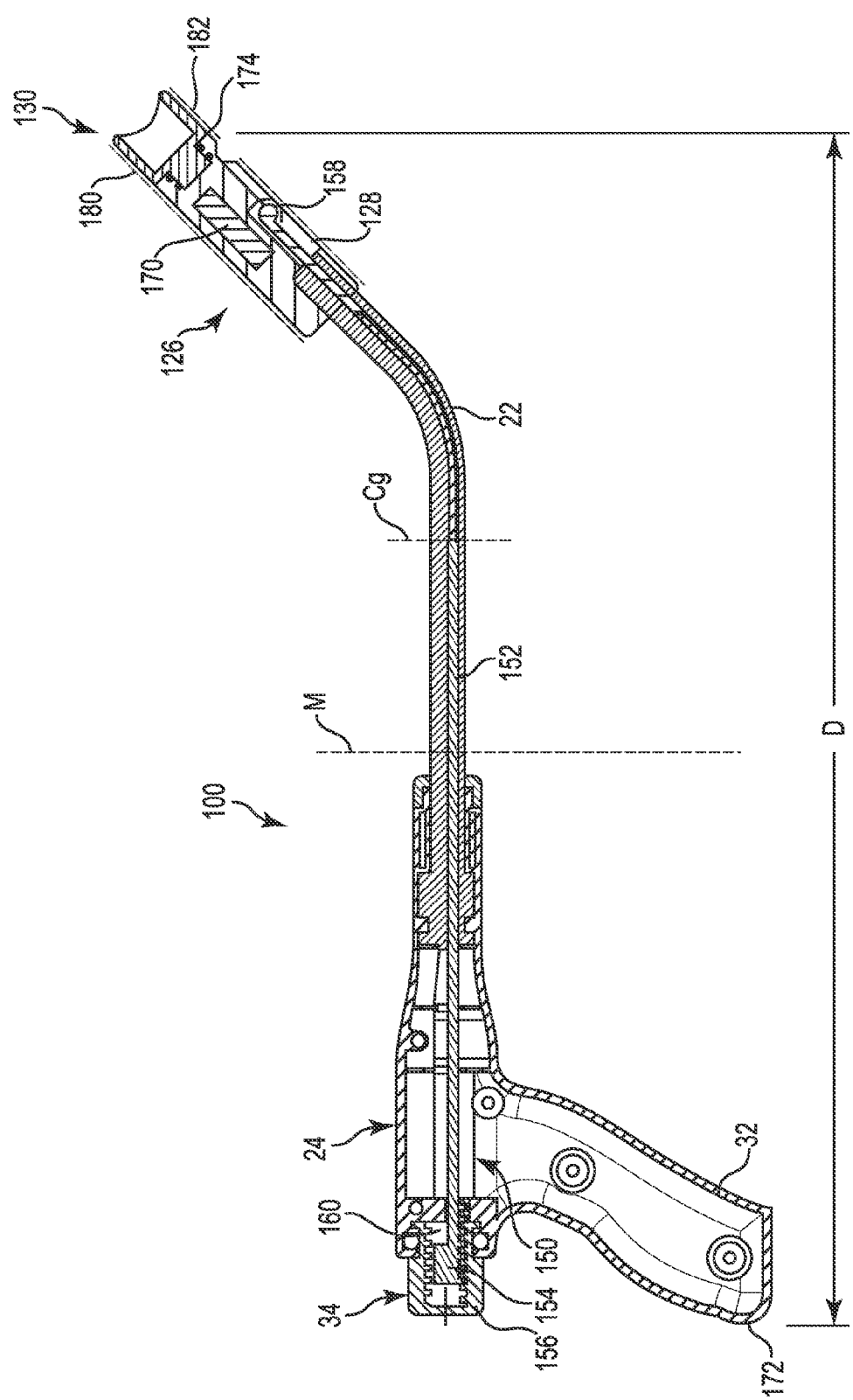
FIG. 11 is a cross-sectional view of one embodiment of a vaginal manipulator.

FIG. 11 is a cross-sectional view of one embodiment of a vaginal manipulator 100. The vaginal manipulator 100 (manipulator 100) includes the shaft 22 and the handle 24 described above. The shaft 22 is connected between the handle 24 and a head 126 that is attachable to a head extender 130. A door 128 is attached to the head 126 at a pivot point and operates in a similar fashion to the door 28 described above.

The actuator 34 is provided to move the door 128 in a direction that pivots away from the head 126 and retracts back to the head 126 to create a smooth surface. In one embodiment, the actuator 34 includes a mechanism 150 connected between the handle 24 and the door 128 that includes a rod 152 with a proximal end 154 connected to a knob 156 and a distal end 158 attached to the door 128. In one embodiment, the proximal end 154 is threaded to provide a worm gear that meshes/threads with gears formed inside of the knob 156. The knob 156 is secured to the handle 24 by a flange 160 that allows the knob 156 to rotate without changing its longitudinal position. In this manner, rotation of the knob 156 translates to axial longitudinal movement of the rod 152 that operates to move the door 128 relative to the head 126.

In one embodiment, the head 126 is a weighted head and includes a weighted insert 170. The weighted insert 170 is provided to shift a center of gravity of the manipulator 100 toward the head 126. For example, in one embodiment the manipulator 100 has a device length D extending from a proximal end 172 of the handle 24 to a distal end 174 of the head 126. A midpoint M of the manipulator 100 is located at half of the device length D. The weighted insert 170 shifts a location of a center of gravity Cg of the manipulator 100 to a location between the midpoint M and the head 126. In this manner, the manipulator 100 is "forward weighted" toward the head 126, and this allows the head 126 to remain positioned within the vagina without the surgical assistant having to hold the handle 24. In one embodiment, the weighted insert 170 is selected to shift the center of gravity Cg of the manipulator 100 closer to the head 126 than the center of gravity Cg is to the midpoint M.

In one embodiment, the head 126 is provided with a lubricating coating 180 that allows the head 126 to have reduced friction for placement into the vagina. In one embodiment, the head extender 130 is provided with a lubricating coating 182 that allows the head extender 130 to have reduced friction for placement in the vagina. One suitable lubricating coating is a hydrophilic coating for use as coatings 180, 182 and is available as the HARMONY™ Advanced Hydrophilic Coating available from SurModics, Inc., Eden Prairie, Minn.

Although not illustrated, embodiments of the manipulator 100 include providing the head 126 with the sliding tissue index 400 described above.

FIGS. 12-17 are schematic views of the device 20 employed to internally manipulate an orientation of the vagina V of the patient during a laparoscopic procedure. FIGS. 12-17 represent certain related anatomy but are not drawn to scale. The laparoscopic procedure may be of the robotically-assisted type of laparoscopic procedure. The device is suited for manual use in dissecting tissues off of the vagina V and in manipulating the orientation of the vagina V. Although features of a laparoscopic vaginal procedure are described below, it is to be understood that the device 20 is suitable for manually manipulating the vagina or other organs in other surgical procedures, including other robotic procedures and the like.

Figure 12:
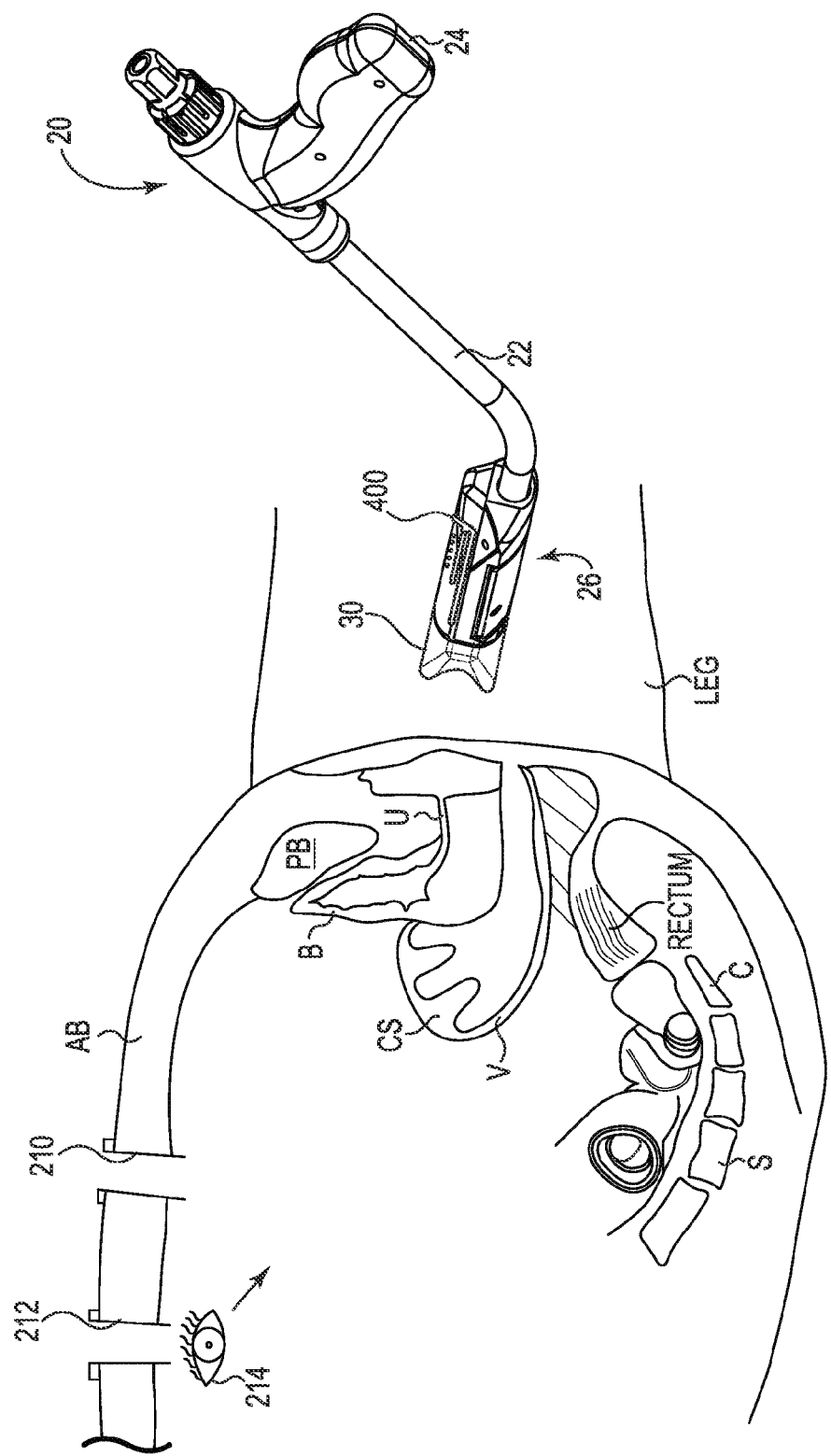
FIG. 12 is a schematic view of the vaginal manipulator illustrated in FIG. 1 employed in a laparoscopic surgical procedure.

FIG. 12 is a schematic view of internal organs of a supine patient with the head 26 of the device 20 in position for insertion into the vagina V. A natural vagina has an entrance and terminates at the cervix, which communicates with the uterus. Some women have their uteruses removed through a hysterectomy, and some of these procedures result in the presence of a cervical stump CS connected to the vagina V as illustrated. The head extender 30 is configured to accommodate the presence of either a cervix or the cervical stump CS.

The bladder B communicates with the urethra U and is located anterior to the vagina V and posterior to the pubic bone PB. The digestive tract and the rectum are located posterior to the vagina V. The sacrum S and the coccyx C are located posterior to the digestive tract. The abdominal wall AB protects and supports the internal organs.

During a laparoscopic surgical procedure, one or more access ports are formed through the abdominal wall AB (usually supported by a trocar) to allow a visualization camera and tools to access the internal organs. In the illustrated embodiment, a first trocar 210 provides an access port for surgical tools and a second trocar 212 provides an access port for an optical camera 214. One or more additional ports (for example a nitrogen inflation port) may be provided through the abdominal wall AB in what is traditionally described as a trans-abdominal approach to the vagina V.

Figure 13:
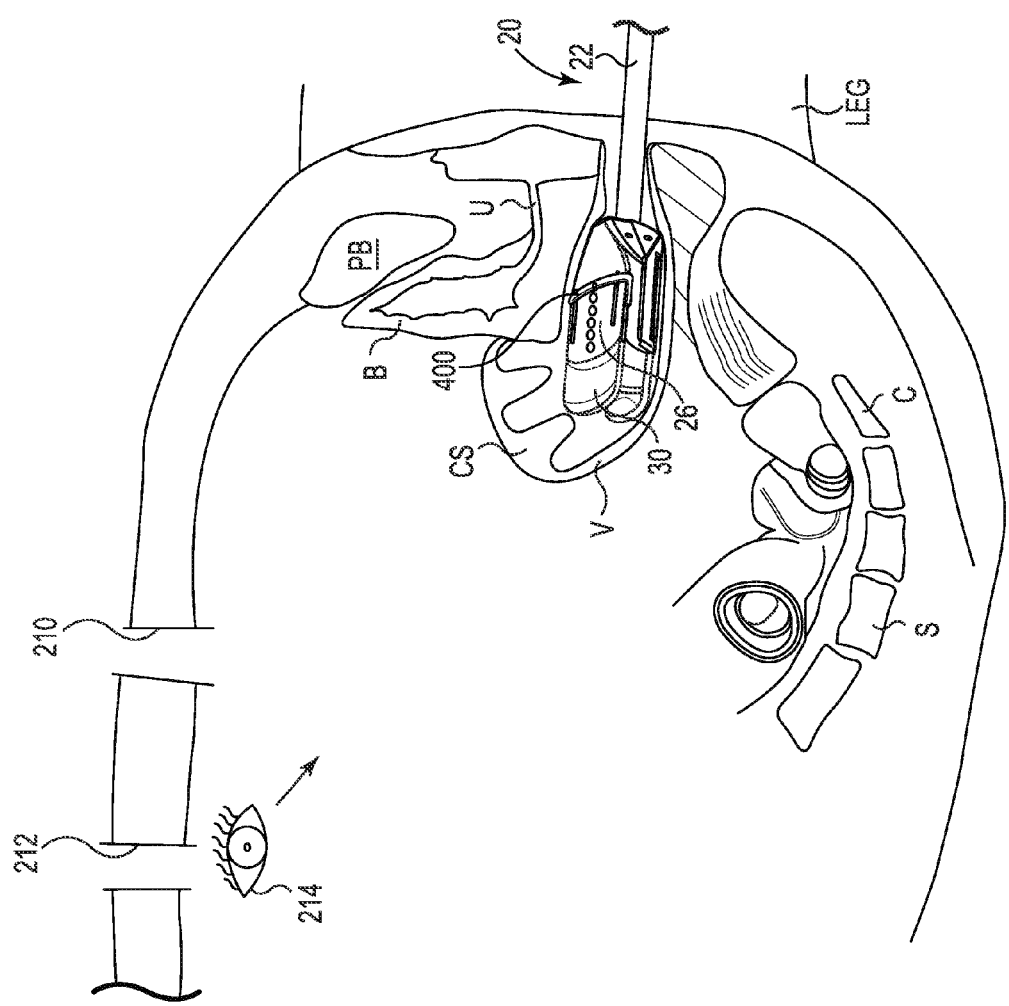
FIG. 13 is a schematic view of the vaginal manipulator illustrated in FIG. 12 inserted into a vagina.
Figure 17:
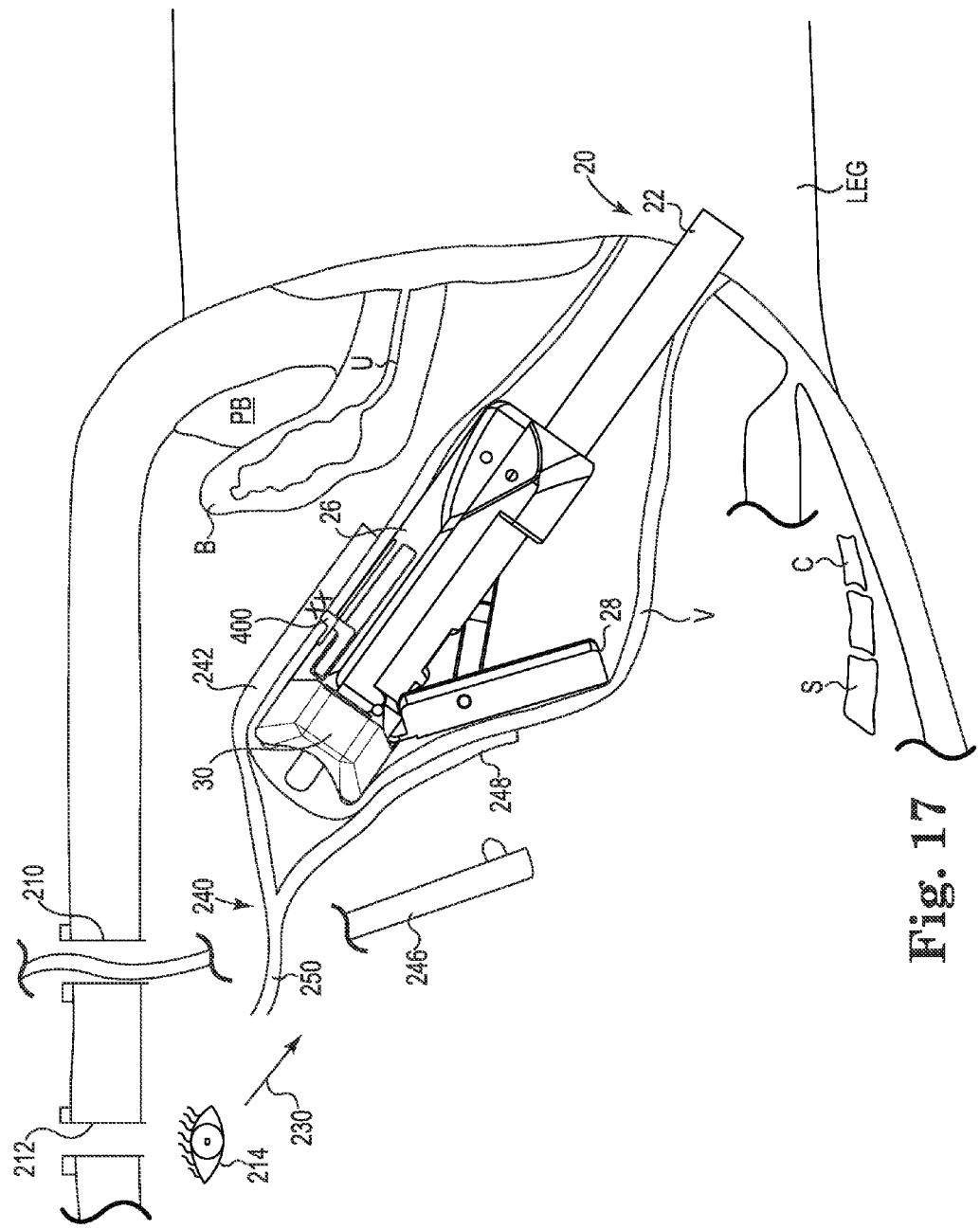
FIG. 17 is a schematic view of the vaginal manipulator illustrated in FIG. 12 employed to attach a support to the vagina in a sacrocolpopexy procedure.

FIG. 13 is a schematic view of the head 26 of the device 20 inserted into the vagina V. The shaft 22 is operable to allow the surgeon to manipulate the head 26/extender 30 and control the orientation of the vagina V, which is useful when dissecting tissues away from the vagina V (FIG. 12) and when attaching support material to the vagina V (FIG. 17). In some embodiments, the shaft 22 is rigid and allows the surgeon to use the shaft 22 as a lever to move and orient the vagina V to assist in tissue dissection or in presenting a wall of the vagina V for visualization by the camera 214. Movement and use of the device 20 is assisted by the camera 214.

Figure 14:
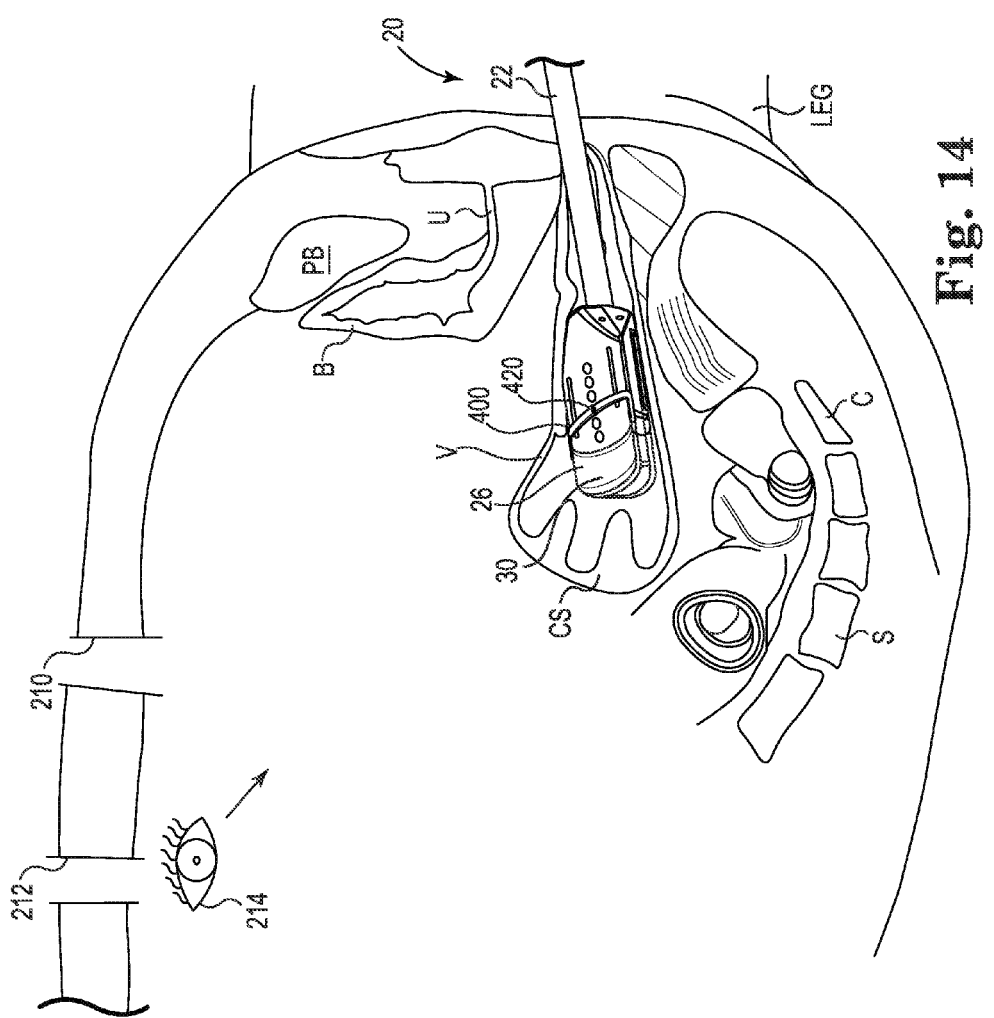
FIG. 14 is a schematic view of the vaginal manipulator illustrated in FIG. 12 assisting in the dissection of vesicovaginal tissue.

FIG. 14 is a schematic view of the device 20 employed to dissect vesico-vaginal tissue away from a wall of the vagina V. One or more surgical tools are inserted through the trocar 210 toward the vagina V. The surgeon moves the head 26 of the device as controlled by the shaft 22 to displace portions of an anterior wall of the vagina V, which allows the surgeon to progressively dissect the vesico-vaginal tissue from between the bladder B and the vagina V. It is desirable to expose the anterior wall of the vagina V to allow the surgeon to optimally orient the vagina V when addressing prolapse and in improving support provided to the vagina V, for example during a sacrocolpopexy procedure.

The sliding tissue index 400 provides a guide to indicate to the surgeon how far back (or proximal) that tissue should be dissected off of the outer wall of the vagina from the vagina apex or cervical stump CS. The presence of the rib 420 is visible laparoscopically through the vaginal tissue when viewed by the camera 214, which allows the surgeon to selectively dissect an appropriate amount/length of tissue off of the outer wall of the vagina V to prepare the vagina for attachment of support material thereto. For example, the surgeon might desire to fix a 6 cm length of support material to the vagina and will adjust the rib 420 of the tissue index 400 to a location 6 cm from the leading distal edge of the head 26 (or extender 30). The surgeon then dissects the vesico-vaginal tissue away from the exterior wall of the vagina V up to the rib 420 to expose 6 cm of the exterior wall of the vagina for reception of the support material. The presence of the rib 420 is also tactilely identifiable through the vaginal tissue, which allows the surgeon to feel the presence of the rib 420, for example with a tool introduced laparoscopically through the abdomen.

The head extender 30 allows the surgeon to dissect anterior tissue of the vagina V while using a portion of the head 26 as a backboard for the anterior tissue. The head extender 30 attached to the head 26 permits full extension of the vagina V by imparting force to the apical area of the vagina V. For some patients, extension of the apex of the vagina V might result in some of the anterior tissue being located proximally beyond the head 26, and thus unsupported. The head extender 30 increases the length of the head 26 to ensure that the anterior tissue is supported internally by the head 26.

Figure 15:
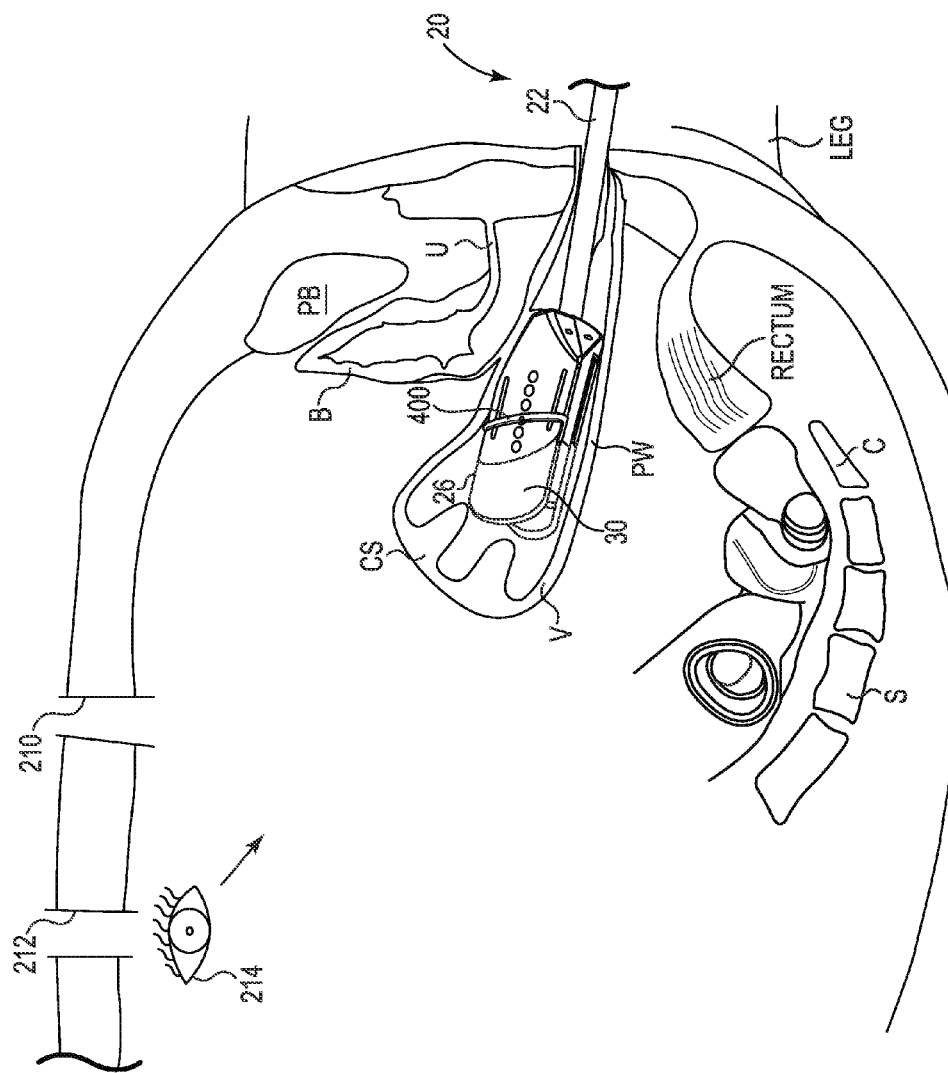
FIG. 15 is a schematic view of the vaginal manipulator illustrated in FIG. 12 assisting in the dissection of rectovaginal tissue.

FIG. 15 is a schematic view of the device 20 employed to dissect recto-vaginal tissue away from a wall of the vagina V. The surgeon employs the shaft 22 to provide a lifting force to the vagina V as suitable other tools are employed to dissect the recto-vaginal tissue from between a posterior wall PW of the vagina V and a sheath or other tissue layers attached to the rectum. Although not shown, the device 20 is also useful for manipulating the vagina V to allow the surgeon to relieve the uterosacral ligament and to access and relieve other connective tissues attached between the vagina V and other organs.

In one embodiment, the recto-vaginal tissue is dissected away from the posterior wall of the vagina V to the same extent as the vesico-vaginal tissue was removed from the anterior wall of the vagina V, which as noted above assisted through the guidance of the tissue index 400.

Figure 16:
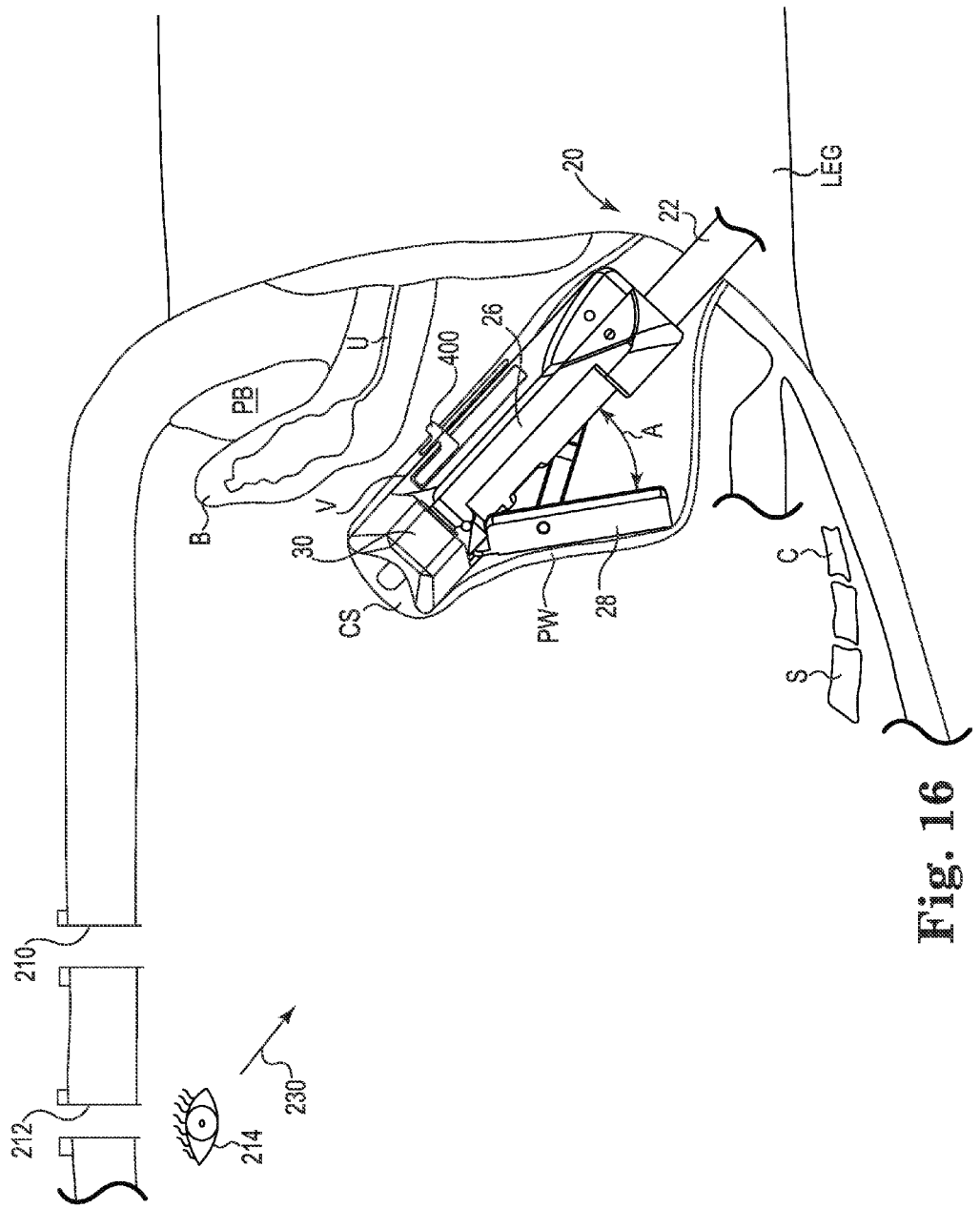
FIG. 16 is a schematic view of the door of the vaginal manipulator illustrated in FIG. 12 deployed to provide a view of a posterior wall of the vagina.

FIG. 16 is a schematic view of the vagina after the anterior wall and the posterior wall PW of the vagina V have been separated from the bladder/rectal connective tissue, respectively. The pocket 94 formed in the distal end 62 of the extender 30 is engaged with the cervical stump CS.

The posterior wall PW of the vagina V, and in particular, the distal posterior wall PW of the vagina V in the direction of the vaginal opening, is typically impeded by other tissues and hidden from the view of the surgeon during laparoscopic surgery. Some tools, such as the uterine manipulator marketed as the RUMI® II System available from Cooper Surgical of Trumbull, Conn., provide a static device that is insertable into the vagina and/or the uterus. Such tools do not provide a view of the distal posterior wall PW of the vagina V.

In contrast, the kick-out door 28 of the head 26 is independently movable through activation of the actuator 34 and its movement mechanism to provide a fully visible view of all portions of the posterior wall PW of the vagina V. In the illustrated embodiment, the door 28 has been pivoted away from the head 26 to move (or "kick out") the posterior wall PW of the vagina V into the line of sight 230 of the camera 214 that is positioned trans-abdominally. The door 28 of the head 26 moves independently to allow the surgeon to advantageously position the posterior wall PW of the vagina V into full visual sight of the camera 214.

FIG. 17 is a schematic view of the device 20 employed to attach a support 240 to the vagina V in a laparoscopically-assisted sacrocolpopexy procedure. One suitable support 240 is a Y-shaped sacrocolpopexy support fabric identified as Restorelle™ available from Coloplast Corp., Minneapolis, Minn. having leg portions 242, 248 diverging away from a tail portion 250.

The patient is prepared for surgery and is usually supine. The access ports are formed in the abdominal wall AB and supported by the trocars 210, 212. The head 26 and extender 30 of the device 20 is inserted into the vagina V to assist in dissecting the vesico-vaginal and recto-vaginal tissues away from the walls of the vagina V as described above.

The door 28 is movable to orient the posterior wall PW of the vagina V into the view of the camera 214, which assists the surgeon in attaching the second leg portion 248 of the support 240 to the posterior wall PW of the vagina, for example through the use of the suture tool 246. The head 26 and the extender 30 are useful in orienting the vagina V into a desired support-position as the tail 250 of the support 240 is secured to the sacrum S. The attachment of the support 240 to the vagina V supports and surgically corrects the prolapse of the vagina V, or suitably positions the vagina V into a desired anatomical position after removal of the uterus.

The tissue index 400 provides a rib 420 or a bump that is visible through the laparoscope and in some cases even through the wall of the vagina V. In one embodiment, the leg portion 242 of the support 240 is attached to the anterior wall of the vagina V, and the location of the placement of the sutures through the support 240 is guided by the tissue index 400.

Figure 18:
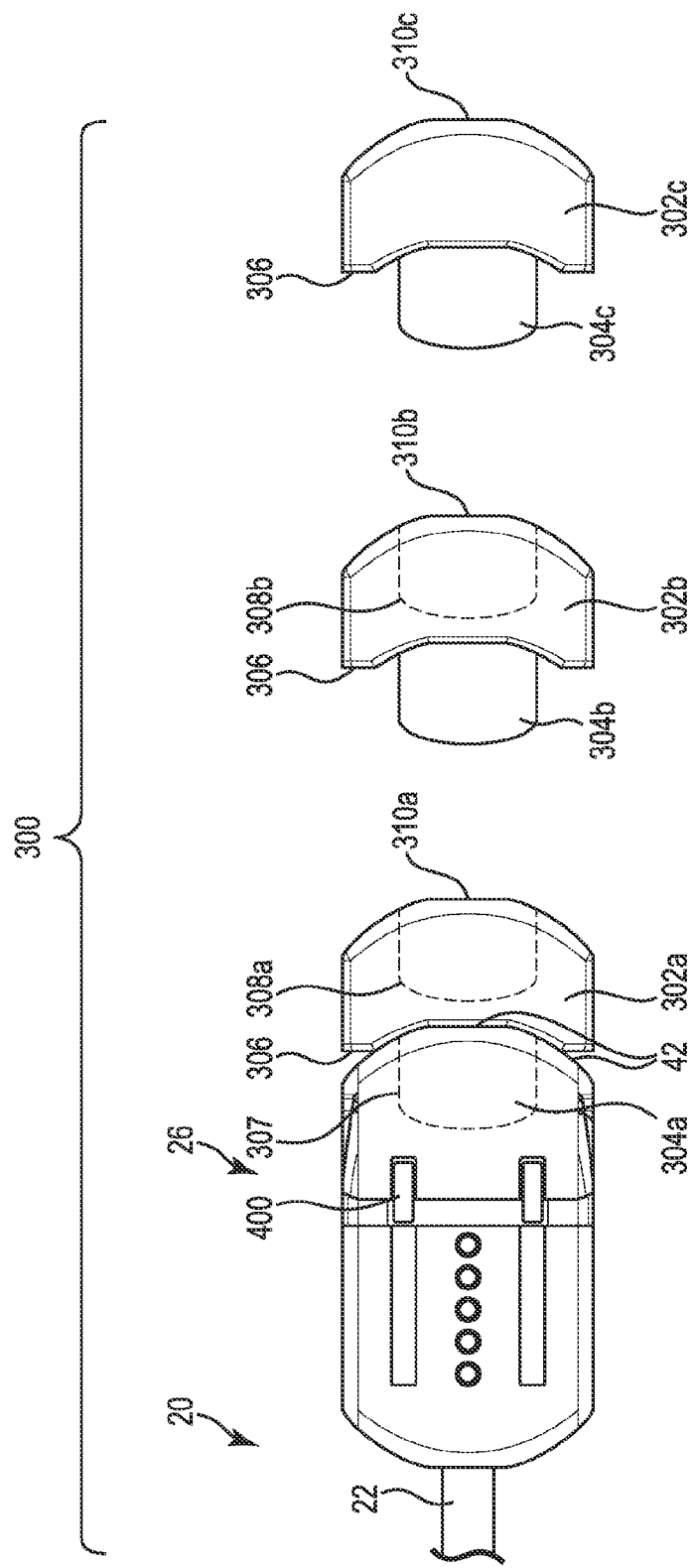
FIG. 18 is a top view of a kit including the vaginal manipulator illustrated in FIG. 1 provide with multiple head extenders.

FIG. 18 is a top view of a kit 300 including the vaginal manipulator 20 and a plurality of head extenders 302a, 302b, and 302c. The shaft 22 and the head 26 of the manipulator 20 described above is illustrated. The head extenders 302a, 302b, and 302c are attachable to the head 26 to extend the length and augment the maneuverability of the head 26.

Each head extender 302a, 302b, and 302c includes a post 304a, 304b, 304c, respectively, extending from a proximal end 306 of the head extender 302. In general, the post 304a, 304b, or 304c is removably insertable into an opening 307 formed in either the distal end 42 of the head 26 or an opening 308 formed in a distal end 310 of a mating one of the plurality of the head extenders 302a or 302b. In this manner, a suitable numbers of the head extenders 302a, 302b, and 302c can be selected by the surgeon and connected together to achieve a desired extended length of the head 26.

In the example shown, the post 304a of one of the head extenders 302a is attached to the opening 307 formed in the head 26 to extend a length of the head 26. The post 304b of an additional head extender 302b is attachable to the opening 308a formed in the head extender 302a to further extend the reach and the maneuverability of the device 20. The post 304c of an endmost head extender 302c is attachable to the opening 308b formed in the head extender 302b. In one embodiment, the endmost head extender 302c has no opening formed in its distal end 310c of the endmost head extender, which provides a uniform "backboard" surface that facilitates control of the apex of the vagina during sacrocolpopexy procedures. Such an endmost head extender 302c has utility in cases where the patient has had a hysterectomy with the entire cervix removed.

In one embodiment, both the opening 307 formed in the distal end 42 of the head 26 and the opening 308 formed in the distal end 310 of the mating one of the plurality of the head extenders 302a, 302b are formed to be cervical cup openings sized for engagement over a cervical fornix. The cervical cup openings, as an example, are formed to have a similar size and shape as the compound curvature and opening illustrated and described in FIGS. 5 and 6 above.

In one embodiment, each of the head extender 302a, 302b, and 302c has an approximately uniform length of about 2 cm between the proximal end 306 and the distal end 310. In one embodiment, each of the head extender 302a, 302b, and 302c is provided with a different length between the ends 306, 310. In one embodiment, the head extenders 302a, 302b, and 302c are adapted to be connected together (e.g., "mixed and matched") to achieve a desired length of additional head extension, as determined by the surgeon.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A vaginal manipulator comprising:
   a head having a first end connected to a shaft and a distal end opposite of the first end, an anterior side opposite a posterior side, a first lateral edge, and a second lateral edge on an opposite side of the head from the first lateral edge;
   a tissue index disposed laterally across the anterior side of the head and coupled with the first lateral edge and the second lateral edge of the head;
   a door having a pivot portion attached to a distal portion of the head and a free portion that is movable away from the head, where the door has a posterior surface that is configured to reduce or prevent the head from pinching tissue when the head is inserted into a vagina; and
   a head extender attachable to the distal end of the head.

2. The vaginal manipulator of claim 1, wherein the free portion of the door is movable away from the first end of the head.

3. The vaginal manipulator of claim 1, wherein the door is posterior of the posterior side of the head.

4. The vaginal manipulator of claim 1, further comprising: a handle connected to a proximal end of the shaft.

5. The vaginal manipulator of claim 1, further comprising:
   a handle connected to a proximal end of the shaft;
   wherein the shaft is curved to locate the anterior side of the head closer to the handle than the posterior side of the head is to the handle.

6. The vaginal manipulator of claim 1, wherein the shaft is a rigid shaft that is fabricated to plastically deform at a bending force of 20 pounds.

7. The vaginal manipulator of claim 1, wherein the head extender has a post that is insertable into an orifice formed in the distal end of the head.

8. The vaginal manipulator of claim 1, wherein the head extender has a post that engages with an orifice formed in the distal end of the head such that the head extender is attachable to and removable from the head.

9. The vaginal manipulator of claim 1, wherein a distal end of the head extender is configured to engage with a cervix associated with the vagina.

10. The vaginal manipulator of claim 1, wherein the tissue index slides relative to the head.

11. The vaginal manipulator of claim 1, wherein the distal end of the head extender has a compound curvature formed by a concave curvature that intersects with a convex curvature.

12. The vaginal manipulator of claim 11, wherein the combination of the head, the tissue index, the door, and the head extender is sized for insertion into the vagina to allow the door to manipulate the posterior wall of the vagina as the head extender engages the apex of the vagina and as the tissue index provides a visual indicator in an anterior wall of the vagina.

13. The vaginal manipulator of claim 1, wherein the head includes a weighted insert.

14. A vaginal manipulator comprising:
   a head having a first end connected to a shaft and a distal end opposite of the first end;
   a tissue index disposed laterally across the head, the tissue index adapted to slide in a longitudinal direction between the first end and the distal end of the head;
   a door having a pivot portion attached to a distal portion of the head and a free portion that is movable away from the head; and
   a head extender including a post that is insertable into an orifice formed in the distal end of the head;
   wherein a combination of the head, the tissue index, the door, and the head extender is sized for insertion into a vagina to allow the door to manipulate a posterior wall of the vagina and the head extender to engage an apex of the vagina.

* * * * *